United States Patent

Schmidt et al.

[11] Patent Number: 5,813,277
[45] Date of Patent: Sep. 29, 1998

[54] APPARATUS AND METHOD FOR MEASURING THE TENSILE STRENGTH OF FABRIC

[75] Inventors: Klaus Schmidt, Kaiserslautern; Peter Schmitt, Rodenbach, both of Germany

[73] Assignee: Firma Carl Freudenberg, Germany

[21] Appl. No.: 506,459

[22] Filed: Jul. 25, 1995

[30] Foreign Application Priority Data

Jul. 26, 1994 [DE] Germany ............... 44 26 405.4

[51] Int. Cl.⁶ ..................................... G01N 3/30
[52] U.S. Cl. ..................... 73/159; 73/838; 73/12.13
[58] Field of Search ............... 73/159, 862.391, 73/862.453, 862.42, 838, 840, 12.03, 12.13, 79

[56] References Cited

U.S. PATENT DOCUMENTS

| | | | |
|---|---|---|---|
| 2,748,596 | 6/1956 | Tasker | 73/12.13 |
| 3,160,002 | 12/1964 | Lovette | 73/840 |
| 4,055,071 | 10/1977 | Frazier | 73/12.13 |
| 4,480,487 | 11/1984 | Kunzfeld | 73/862.453 |
| 5,181,739 | 1/1993 | Bauer et al. | 73/862.391 |
| 5,251,492 | 10/1993 | Nowag | 73/862.391 |
| 5,329,822 | 7/1994 | Hartel et al. | 73/862.391 |

FOREIGN PATENT DOCUMENTS

| | | | |
|---|---|---|---|
| 579483 | 7/1959 | Canada | 73/838 |
| 6-160260 | 6/1994 | Japan | 73/12.13 |
| 715692 | 2/1980 | U.S.S.R. | 73/12.13 |

OTHER PUBLICATIONS

Spangler, R.D. and E.B. Cooper, Equipment to measure the energy absorption of films at high strain rates, Jour. App. Phys., vol. 28, p. 329, Mar. 1957.

*Primary Examiner*—Ronald L. Biegel
*Attorney, Agent, or Firm*—Kenyon & Kenyon

[57] ABSTRACT

An apparatus for measuring the tensile strength of a textile fabric comprises a measuring system having electromagnet, a mass capable of being held in place by the electromagnet, a piezoelectric force sensor connected to said mass, and a rounded-off impact body. By de-energizing the electromagnet, the impact body free-falls onto the textile fabric, which is held in place beneath the impact body under tension. The impact force detected by the sensor is converted to a form with which a computer can compute the tensile strength of the fabric. A series of measurements can be made of a length of fabric advanced through the apparatus in successive stages.

4 Claims, 3 Drawing Sheets

APPARATUS AND METHOD FOR MEASURING THE TENSILE STRENGTH OF FABRIC

BACKGROUND OF THE INVENTION

The present invention relates to an apparatus and method for measuring the tensile strength of textile fabrics.

The general protocol for determining the tensile strength of textile and other elastic fabrics is set forth in DIN 53 857 ("Determination of Breaking Force"). In standard tests, the force is measured through the tearing of sample pieces. The internal forces holding together the fabric of the sample pieces is exceeded by the external forces, irreversibly ruining the sample.

This invention is directed to the problem of non-destructively determining the tensile strength of a textile fabric.

SUMMARY OF THE INVENTION

The present invention solves this problem by providing method and apparatus for non-destructively evaluating the tensile strength of fabric. A gripping device is used (i.e., guide elements) to advance a length of fabric (typically taken off a roll) under tension. The fabric passes over a measuring table having a built-in gap that defines a test window. This test window lies immediately beneath a movable impact assembly that is held in position by an electromagnet. The impact assembly has a magnetically attractable mass at one end and a rounded impact body at its other. Interposed between the impact body and the magnetically attractable mass is a piezoelectric force sensor, offset from either end of the impact assembly by colinear connecting members. When the electromagnet is de-energized, the impact assembly falls onto the fabric, causing the sensor to generate a signal indicative of the force of impact, which can be analyzed to determine the strength of the fabric.

BRIEF DESCRIPTION OF THE FIGURES

For a more complete understanding of this invention, reference should now be made to the embodiments illustrated in greater detail in the accompanying drawings and described below. In the drawings.

DETAILED DESCRIPTION

Figure 1:
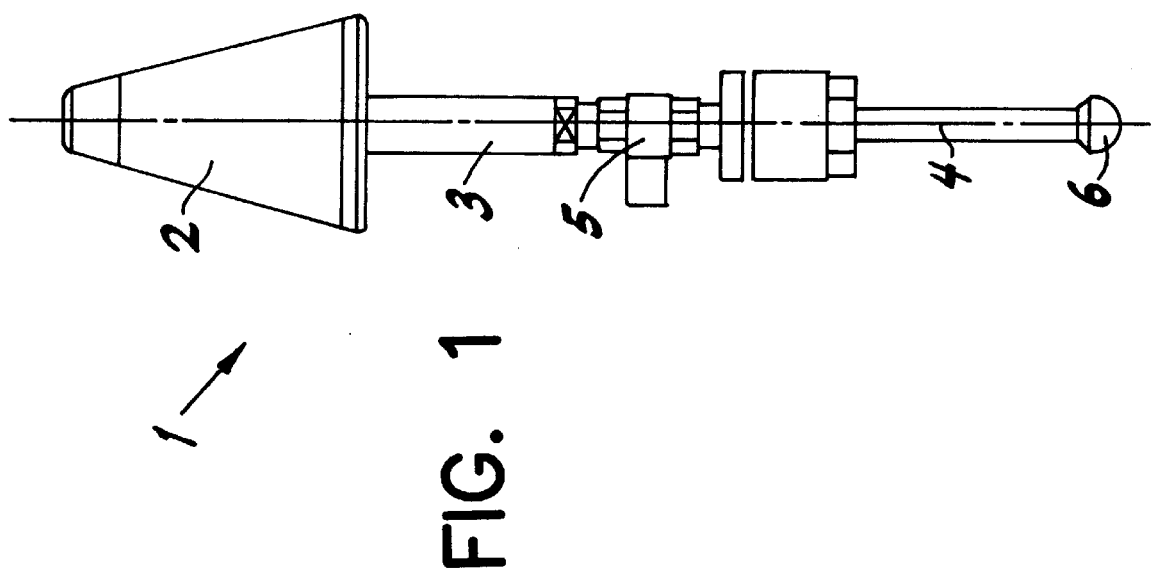
FIG. 1 is a elevational view of the free-falling impact assembly used in the textile measuring system.
Figure 4:
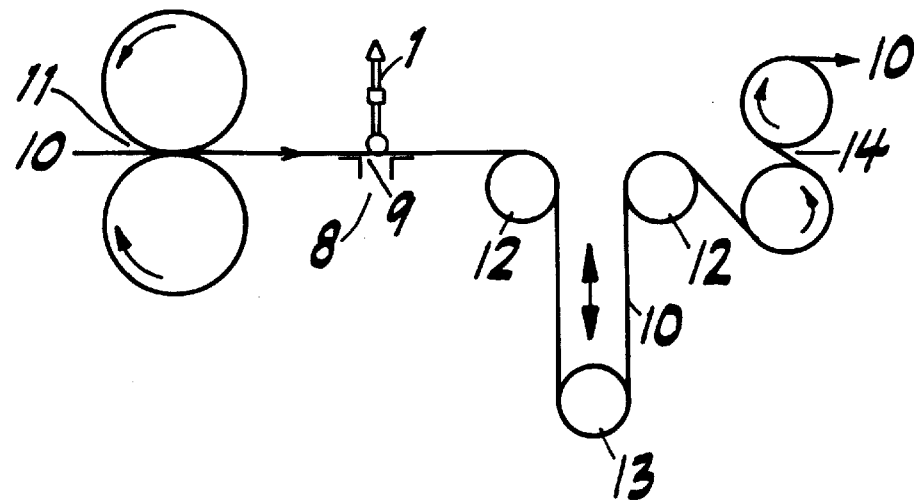
FIG. 4 is a block diagram of the measuring system illustrating a preferred embodiment of gripping devices used to advance and hold a section of textile under tension beneath the impact assembly.

Referring now to the drawings, wherein like numerals indicate like parts throughout, a vertically disposed impact assembly is generally designated 1 in FIGS. 1 and 4, and provides a free-falling assembly to impact a section of textile in a controlled manner. During the course of this impact, a signal representative of the strength of the fabric is generated, as shall be explained below.

Figure 2:
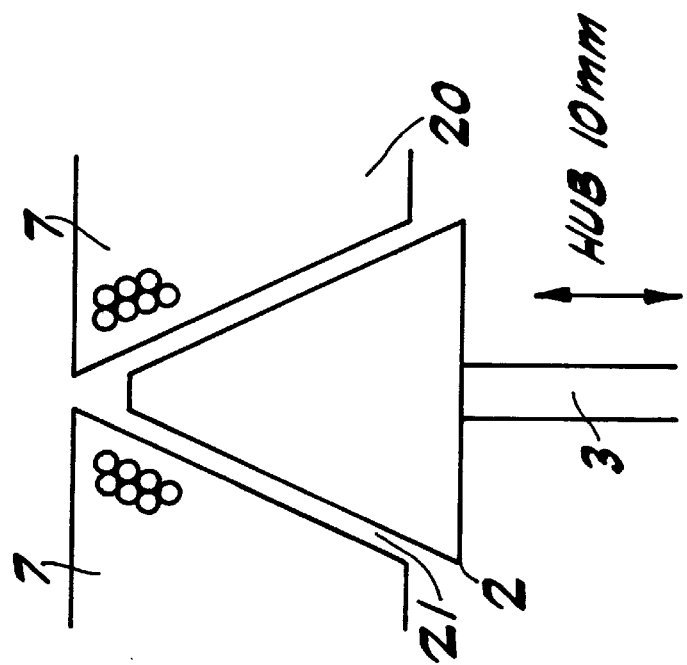
FIG. 2 schematically depicts an arrangement of electromagnets to selectively hold and release the mass of the impact assembly of the measuring system.

The upper section of the impact assembly and relevant details of a mechanism for its selective release from a static position to one in which it free-falls onto a section of textile is illustrated in FIG. 2. The release mechanism comprises an upper, immovable part 20 formed of electromagnets 7 that can be switched on and off. The immovable part 20 is configured to have a conical, downwardly extending opening 21 that opens toward the bottom. In the embodiment shown in FIG. 2, the height of the conical opening is 50 mm.

Figure 3:
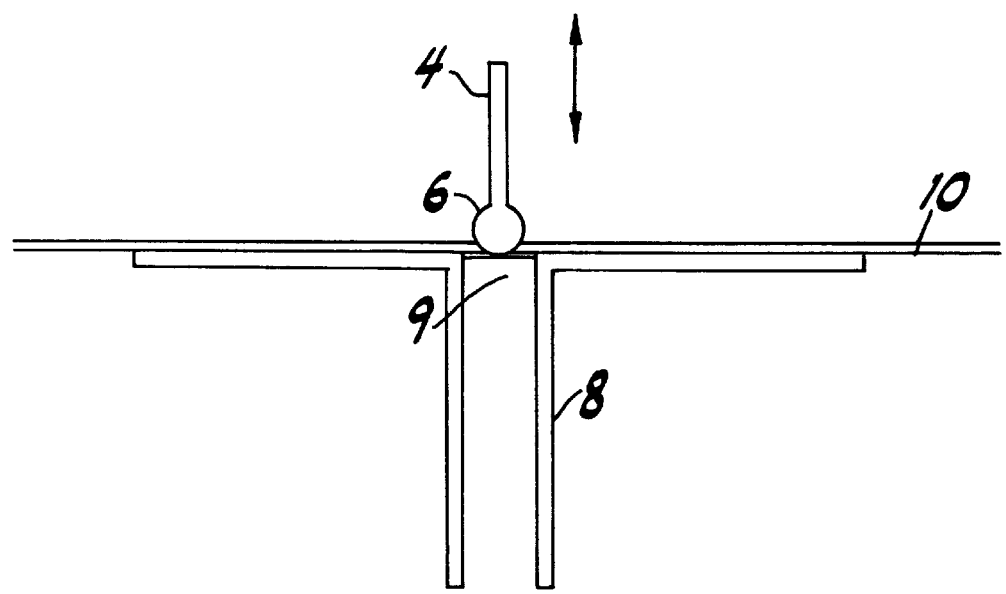
FIG. 3 schematically depicts the cooperation of a measuring table, textile, and impact body.

The impact assembly 1 of the measuring system (FIGS. 1 and 3) is arranged in the vertical direction in cooperation with the electromagnets to provide for the former's controlled fall. As shown in FIG. 1, the moveable assembly has at its upper section a magnetically attractable mass 2 having a weight of 180 to 250 g. This mass 2 is formed as a conic so as to fit into the corresponding cavity 21 of the aforesaid electromagnet within the immovable part 20. The vertically-extending longitudinal axis of the mass 2 is preferably at least 47 mm long so as to permit the mass to fill the cavity 21 of the electromagnets 7 as completely as possible lengthwise.

A first, vertically disposed connecting member 3 having negligible mass, (e.g., an aluminum bar with a maximum length of 40 mm) connects the mass 2 to a piezoelectric force sensor 5 located beneath it. A second, vertically disposed connecting bar 4 similar to the first connecting bar 3 connects the force sensor 5 to an impact body 6 located beneath the force sensor 5. The impact body 6 is designed to strike the central portion of a surface of test fabric 10. The impact body 6 is made of a non-elastic and non-plastic material; its mass should not be more than half the mass of the entire impact assembly 1. The portion of the impact body 6 facing the fabric has a conical or spherical roundness pointing downwards with a radius of from 0.5 mm to 25 mm.

When the electromagnet is de-energized, the impact assembly 1 is released and falls, causing the impact body 6 to strike the test fabric. The resulting impact force is transmitted via the second connecting member 4 to the force sensor 5. The force sensor 5 is of the piezoelectric type; it converts this force into an electrostatic charge signal. The maximum value of this signal is converted in a charge amplifier into a force-proportional voltage signal having the units of volt/newton, and as such is fed to a computer.

The piezoelectric force sensor 5 is composed of a measuring-flat washer which lies between two special nuts and is prestressed by a pivot pin. This gives the flat washer a high level of prestress and, accordingly, a high natural frequency.

Figure 5:
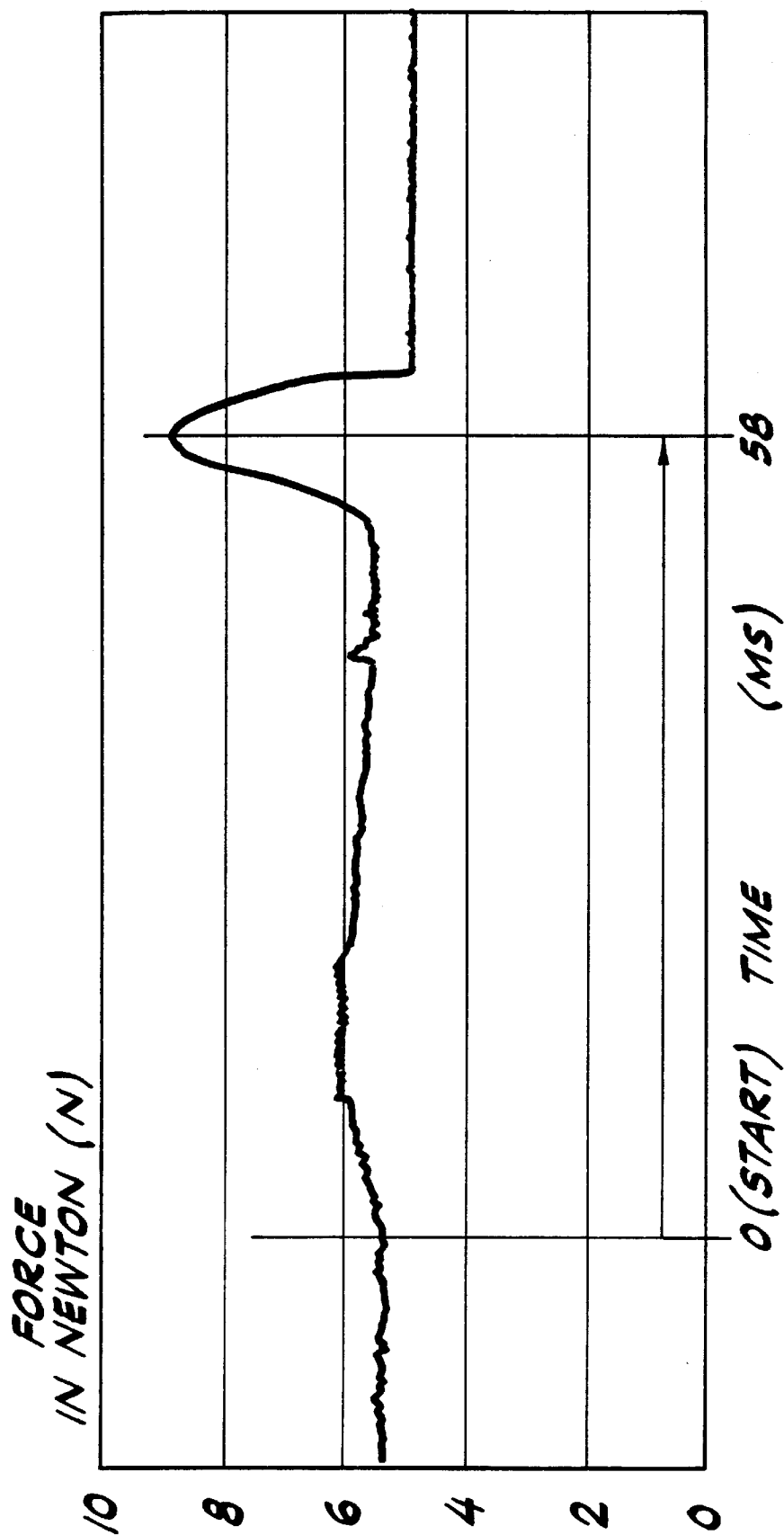
FIG. 5 is a representative force/time diagram obtained by measuring the tensile strength of a fabric using the method and apparatus of the invention.

A computer (not shown here) can be used to determine the tensile strength of the textile fabric 10 as follows. As is shown in FIG. 5, with each contact of the impact body 6 with the textile test fabric 10, the voltage level rises to a maximum and then falls off. The computer determines the maximum value from the voltage levels supplied to it. This maximum level correlates with the tensile strength.

The force-proportional voltage signal is provided as a standardized signal ranging from 0 to 10 volts. This means that the force signal of 0 to 20 Newtons [N] is converted by means of the charge amplifier into a proportional voltage signal of 0 to 10 volts [V]. This voltage signal is converted in the computer by means of an analog signal-processing program to the corresponding force value:

$$F = \left( \frac{20N}{10V} \right) \cdot U$$

Where

F: Force in [N]; and

U: Maximum measured voltage in [V]

Thus, with several measurements over a width of textile, there can be obtained a profile of strength values. By means of a linear regression calculation of these strength values with the tensile strength, which is stated in N/5 cm, a mathematical correlation can be formed between the maximum values and the tensile strength.

For example, consider the example where the data yield a slope of 52 and an intercept of −338 for a textile fabric. The slope of this regression line is expressed in units of N/(5 cm×N), and that of the intercept in terms of N/5 cm. If a force of 10 N is measured, the tensile strength is computed as follows:

Breaking force=F×slope+intercept=10N×52N/(5 cm×N)− 338 N/5 cm=182 N/5 cm.

Gripping apparatus is provided to hold the surface of the textile fabric 10 with a constant tension in a horizontal orientation spaced 10 mm below the position of the impact body 6 as measured when the impact assembly is held in place by the electromagnets 7 above the surface of the textile. The gripping apparatus comprises two elongated guide elements running parallel to each other on opposite sides of that portion of the textile onto which the impact body 6 may fall. The gripping apparatus assures that the measuring surface of the textile fabric 10 is tightly stretched at a constant tension on both sides. The constancy of the gripping is important, because the deformation of the textile measuring surface 6 when struck by the impact body is dependent upon this tension, as too is the force measured by the force sensor 5.

Between the two guide elements and equidistant to them is a measuring table 8 (FIG. 3) which holds the fabric 10 to be tested in a horizontal orientation beneath the impact body 6 and between the guide elements. The measuring table 8 has a gap 9 that is approximately 20 mm wide that defines a window at which the fabric is tested. This window is centered beneath the impact assembly 1. The gap 9 permits the impact body 6 to protrude beneath the plane of the measuring table 8 when the impact assembly 1 is released from the electromagnets 7 and strikes the textile fabric 10.

An embodiment of the apparatus is shown in FIG. 4. It allows the stepwise measuring in rapid succession of tensile strengths of surfaces lying adjacent one another along a width of any length of textile. The entry-side guide member of the gripping device is provided as two calender rolls 11 which have roughened surfaces in order to grip the width of textile 10 without slipping. The calender rolls 11 rotate stepwise in opposite directions as shown.

The delivery-side guide structure, viewed in the transport direction of the fabric 10 from the other side of the measuring table 8 and the gap 9, is composed of a system having two rolls 12 which are capable of rotation. The rolls 12 are horizontally set apart from and parallel to each other, in each case guiding the width of textile 10. Between these rolls is a vertically moveable dancing roll 13 which is arranged parallel to and beneath the aforesaid two rolls 12. The dancing roll 13 has at least triple the mass of the impact assembly 1 of the measuring system.

Downstream from the two rolls 12 and the dancing roll 13 is a double roll 14, also capable of stepwise rotation, and having roll units which do not contact each other. The rolls have a roughened surface (so as to avoid slippage) and guide the textile width 10 in an S-shaped loop.

In the initial step of the operation of the system, the electromagnet 7 is actuated, thereby locking the impact assembly 1 in place in a predetermined position, Next, the textile fabric 10 is axially and horizontally centered 10 mm below the impact body 6 via the gripping device (i.e, the various rolls discussed above), by which it is held with constant tension. The 20 mm wide gap 9 in the measuring table 8 provides a window for the impact body to strike without hitting the table.

The electromagnets 7 are de-energized, enabling the impact assembly 1 and its downwardly pointing impact body 6 to freely fall with a pre-determined impact speed onto the middle of the textile 10 over gap 9. The resulting impact causes a force-proportional voltage signal to be produced via the force sensor 5 and the charge amplifier. This signal is fed to the computer for determination of the tensile strength of the fabric 10.

It is noted that the conical design of the magnets 7 and the correspondingly shaped mass 2 permits the delivery of the impact body 6 from a reproducible starting position accurately centered over the textile surface. Due to the free fall of the impact assembly 1 of the measuring system, frictional forces and other interference effects are effectively eliminated. After measurement is completed and the impact body 6 is resting on the fabric surface, the hollow cone of the electromagnets 7 prevents the mass 2 from tilting, provided the specified dimensions for the height of fall, length of the moveable measuring system-component 1 and longitudinal axes of the cones are configured accordingly.

In a preferred embodiment of the method, successive, identically large surface areas of a textile width 10 of any length are transported in a stepwise manner to the window beneath the impact assembly 1. At each step, a measurement is taken at that fabric surface area (FIG. 4). By thus taking a multitude of individual measurements within a short time, any possibly zonal variation in the tensile strength of a length of fabric can be determined.

In this case, the textile fabric width 10 is stepwise guided during and between the measurements via the entry-side and delivery-side gripping mechanisms, with the impact assembly falling onto the fabric during each interval in which the fabric is stationary.

Thus, initially the fabric width 10 fills up the calender gap between the rolls 11 and is retained there because of the rough surfaces of the rolls. As the fabric is advanced, it stretches on the measuring table 8 across the gap 9 beneath the striking impact body 6.

The textile width 10 is then further guided via two effectively moveable rolls 12 located next to each other on the delivery side, between which the width is pulled downwards by a vertically movable, heavy dancing roll 13. This measure makes it possible to maintain a constant tension of the width 10 across the measuring table gap 9, independent to a high degree of the respective short-term pull which is exerted on either side of the measuring device.

Next, the fabric width is guided along an S-shaped loop about a double roll 14 having two rough, counter-rotating rolls which do not contact one another. This can be followed by a rolling-up device (not shown).

By the stepwise drawing the textile width 10 via the calender 11 across the measuring table 8, the dancing roll 13 and the double roll 14, the adjacent portions of the textile surfaces are successively presented to the impact body 6 for testing.

The downward-pointing surface of the impact body 6, be it conical or elliptical, is rounded, with a radius of curvature of 0.1 mm to 25 mm, depending on the textile material to be tested. With an effective height of fall of 10 mm, an elastic deformation of the surface of the textile fabric being tested of at least (linearly) 3% should occur, i.e, as measured by comparing the deepest point of deformation of the surface at the point of maximum impact with the starting position before the fall of the impact body 6.

In addition, the rounding radius must naturally be of such a size that the impact body does not penetrate the textile on which it impacts (as it otherwise might, for example, when striking a wide-meshed textile), but rather always just non-destructively elastically deforms it. Preliminary tests as may be necessary to determine the suitable rounding and heights of fall are simple to carry out and yield useful empirical parameters within a few minutes.

After their determination, the mass of the freely impact assembly 1 of the measuring system is calculated, it being determined in test series at which values the deformation of the textile surface to be tested amounts to at least 3% without the test material 10 being destroyed. These preliminary tests can be performed in a short period of time.

Use of the apparatus and method of the invention permits the non-destructive and rapid measurement of the tensile strength of a textile sample; the statistical scattering of measured values because of sample change is also avoided: After each measurement, the same sample can be tested again shortly following at the same spot by raising the impact assembly 1 to its reproducible starting position and re-releasing it again. Furthermore, by the utilization of the free fall, frictional influences of the arrangement are avoided.

What is claimed is:

1. An apparatus for determining the tensile strength of a textile fabric, comprising:
    a stationary electromagnet that can be selectively energized, said electromagnet having a downwardly opening cavity that is conical in shape, said conical cavity having a height of approximately 50 mm;
    an impact assembly comprising
        a magnetically attractable mass having a weight of approximately 180 to 250 grams that corresponds in shape to the conical cavity of the electromagnet so as to fit into that cavity, said mass having an axial length of at least approximately 47 mm;
        a piezoelectric force sensor that provides an electrostatic charge signal in dependence upon the degree to which it is mechanically loaded;
        a first vertically extending rigid 19 connecting member no more than 40 mm in length, said connecting member being coaxial with the magnetically attractable mass, said first connecting member being rigidly connected to the mass at a first end and to the force sensor at its other end;
        an impact body and a second rigid connecting member coaxial with the first connecting member joining the force sensor to the impact body, said second connecting member being no more than 40 mm in length, wherein the impact body is made of a non-elastic and non-plastic material making up at most half the mass of the impact assembly, the portion of the impact body facing away from the force sensor having a conical or spherical rounding having a radius of curvature of approximately from 0.5 mm to 25 mm;
    a gripping apparatus for holding the surface of the textile fabric that is to be measured with a consistent tension in a horizontal orientation approximately 10 mm beneath the impact body, said gripping apparatus comprising:
        elongated guide elements running parallel to one another located on both sides of the fabric over which the impact assembly is situated;
        a measuring table located between the guide elements and beneath the impact body, said measuring table supporting the textile fabric in a horizontal configuration and having a 20 mm wide gap beneath the impact body;
    wherein the sensor provides a signal representative of the force with which the impact body strikes the textile fabric when the electromagnet is de-energized, from which the underlying tensile strength of the fabric can be determined by means of a linear regression calculation.

2. An apparatus as set forth in claim 1, wherein the guide elements of the gripping apparatus comprise:
    a calender capable of stepwise rotation for holding a width of textile fabric of any length, said calender having textured surfaces to prevent the fabric from slipping between the rolls, wherein the calender feeds fabric towards the gap in the measuring table; and
    delivery side guide elements located on the opposite side of the gap from the calender, said delivery side guide elements comprising
        two parallel rolls which are capable of rotation that are horizontally set apart from each other;
        a vertically moveable dancing roll located between and parallel to the two parallel rolls, said dancing roll having at least triple the mass of the measuring assembly;
        a double roll downstream from the two parallel rolls, said double rolls being capable of stepwise rotation and having roughened surfaces, wherein the double roll is configured to guide a width of textile without slippage in an S-shaped loop.

3. A method for measuring the tensile strength a textile fabric, comprising the steps of:
    positioning an impact assembly having a magnetically attractable mass at one end, an impact body at its other end, and a force sensor over a length of fabric;
    holding the impact assembly in a selectively energizable electromagnet by energizing the electromagnet;
    positioning and gripping fabric under constant tension horizontally approximately 10 mm beneath the impact assembly;
    de-energizing the electromagnet, thereby permitting the impact assembly to fall onto the fabric;
    measuring the maximum value of a signal from the sensor converted in a charge amplifier into a force-proportional voltage signal proportional to the forces encountered during the impact with the textile fabric; and
    computing the tensile strength of the textile fabric.

4. A method as set forth in claim 3, wherein the textile fabric to be measured is stretched and guided to an area beneath the impact body in a step wise manner and, each time the fabric pauses in its step-wise advance, striking the fabric with the impact body and taking another measurement.

* * * * *